United States Patent [19]

Martel et al.

[11] 4,206,124

[45] Jun. 3, 1980

[54] EPIMERIZATION PROCESS

[75] Inventors: Jacques Martel, Bondy; Jean Tessier, Vincennes; André Teche, Nanterre, all of France

[73] Assignee: Roussel Uclaf, Paris, France

[21] Appl. No.: 18,308

[22] Filed: Mar. 7, 1979

[30] Foreign Application Priority Data

Mar. 17, 1978 [FR] France .................................. 78 07779

[51] Int. Cl.$^2$ ............................................ C07D 307/93
[52] U.S. Cl. ............................ 260/343.3 R; 260/465 F
[58] Field of Search ..................... 260/343.21, 343.3 R, 260/465 D

[56] References Cited

U.S. PATENT DOCUMENTS

| 3,786,070 | 1/1974 | Martel et al. ..................... 260/343.21 |
|---|---|---|
| 3,922,286 | 11/1975 | Yoshioka et al. .............. 260/343.3 R |
| 3,989,654 | 11/1976 | Honda et al. ................ 260/343.21 X |
| 4,014,918 | 3/1977 | Martel .......................... 260/343.21 X |
| 4,132,717 | 1/1979 | Roman ............................. 260/343.21 |
| 4,133,826 | 1/1979 | Warnant et al. .................. 260/465 D |

Primary Examiner—Dolph H. Torrence
Attorney, Agent, or Firm—Hammond, Littell, Weissenberger and Muserlian

[57] ABSTRACT

A novel process for the preparation of (1R,5S) 6,6-dimethyl-4(R)-[(S)-cyano-(3'-phenoxy-phenyl)-methoxy]-3-oxabicyclo-(3-1-0)-hexan-2-one which is an intermediate for the preparation of (S)α-cyano-3-phenoxybenzyl alcohol.

4 Claims, No Drawings

4,206,124

EPIMERIZATION PROCESS

STATE OF THE ART

Copending, commonly assigned U.S. patent application Ser. No. 973,791 filed Dec. 28, 1978 describes the reaction of (R,S)α-cyano-3-phenoxy-benzyl alcohol with the lactone of cis 2,2-dimethyl-3-S-(hydroxymethyl)-cyclopropane -1R-carboxylic acid in an acid medium to form a mixture of (1R,5S) 6,6-dimethyl-4(R)-[(S)-cyano-(3'-phenoxy-phenyl)-methoxy]-3-oxa-bicyclo-(3-1-0)-hexan-2-one and (1R,5S) 6,6-dimethyl-4(R)-[(R)-cyano-(3'-phenoxy-phenyl)-methoxy]-3-oxa-bicyclo-(3-1-0)-hexan-2-one and also describes the separation of the two diastereoisomeric ethers by physical processes such as crystallization or chromatography and individual hydrolysis of the ether to obtain either(S) or (R)α-cyano-3-phenoxy-benzyl alcohol.

When the separation of two diastereoisomers in a composition resulting from such an etherification is effected by physical means, the weight of each diastereoisomers that can be recovered from the etherification mixture is that amount initially present in the mixture and when the racemic α-cyano-3-phenoxy-benzyl alcohol is etherified, the resulting mixture is the predictable equimolar mixture of the diastereoisomer. Therefore, the amount of the individual diastereoisomer that can be recovered by physical separation can never exceed half the weight of the initial mixture without an isolation treatment. Related prior art includes also U.S. Pat. No. 4,133,826.

OBJECTS OF THE INVENTION

It is an object of the invention to provide an improved process for the recovery of (1R,5S) 6,6-dimethyl-4(R)-[(S)-cyano-(3'-phenoxy-phenyl)-methoxy]-3-oxa-bicyclo-(3-1-0)-hexan-2-one.

This and other objects and advantages of the invention will become obvious from the following detailed description.

THE INVENTION

The novel process of the invention comprises treating a mixture of (1R,5S) 6,6-dimethyl-4(R)-[(S)-cyano-(3'-phenoxy-phenyl)-methoxy]-3-oxa-bicyclo-(3-1-0)-hexan-2-one and (1R,5S) 6,6-dimethyl-4(R)-[(R)-cyano-(3'-phenoxy-phenyl)-methoxy]-3-oxa-bicyclo-(3-1-0)-hexan-2-one with a basic agent in an organic solvent in which (1R,5S) 6,6-dimethyl-4(R)-[(S)-cyano-(3'-phenoxy-phenyl)-methoxy]-3-oxa-bicyclo-(3-1-0)-hexan-2-one is insoluble and recovering the latter which will be referred to hereinafter as compound A and the other isomer is compound B.

The preferred basic agents are ammonium hydroxide, amines such as triethylamine, diethylamine, morpholine, piperidine and pyrrolidine or catalytic amounts of an alkali metal hydroxide such as sodium hydroxide and potassium hydroxide, an alkali metal hydride, an alkali metal alkanolate or an alkali metal amide. Most preferred is triethylamine.

The preferred organic solvents for use in the process are lower alkanols of 1 to 6 carbon atoms with isopropanol being preferred.

The process of the invention is a physical separation of the desired diastereoisomeric ether as was the prior art but physical separation is applied to a mixture of diastereoisomeric ethers placed voluntarily in a chemical medium selected to permit a continous and appropriate evolution of the composition of the mixture resulting from the etherification reaction. The chemical medium is selected to permit the obtention in the soluble phase of a mutual stereoconversion to one diastereoisomer into the other (compound A $\rightleftarrows$ compound B), the epimerization of benzyl chiral center being obtained by the action of the basic agent, the proportions of compounds A and B, once equilibrium is attained, being determined by the equilibrium conditions, namely solvent, base and temperature and being generally different from the starting proportions.

The chemical medium, on the other hand, is selected to obtain, moreover, insolubility only of compound A so that in proportion to the amount of compound A eliminated from the reaction medium by insolubilization, the stereoconversion of compound B to compound A in the soluble phase in a basic medium is effected. As compound A is formed from compound B, a new insolubility occurs causing a displacement of the equilibrium again so that there is a progressive transformation of compound B into compound A. Certainly, the more insoluble compound A is in the reaction medium, the higher is the conversion of compound B into compound A.

When in the process of the invention, only the diastereoisomer B is used, in the absence of a spontaneous crystallization of compound A it is necessary to release and achieve the stereo conversion by adding a few seed crystals of diastereoisomer A to begin the epimerization process.

The process of the present invention is similar to the process described in commonly assigned U.S. Pat. No. 4,133,826 and permits the obtaining of ethers of (S)α-cyano-3-phenoxy-benzyl alcohol (esters in said patent) which do not contain the resolved alcohol in an amount greater than that present in the starting mixture of (R) and (S) ethers (esters in the patent). Under these identical operating conditions, it is understood that the lactone of Cis 2,2-dimethyl-3R-hydroxymethyl-cyclopropane-1S-carboxylic acid which is antipodal to that desired may be used to obtain diastereoisomer of the alcohol of (S) configuration to obtain in the process of the invention diastereoisomer crystallization antipodal to compound A and containing the alcohol of configuration (R) [compound B].

The process of the invention is particularly advantageous because of its simplicity and unexpected yields which correspond to the obtention of a diastereoisomeric ether in quantities greater than present in the starting diastereoisomeric ether mixture.

With regard to the diastereoisomeric esters of U.S. Pat. No. 4,133,826, the diastereoisomeric ethers of the present invention have a very important advantage, namely that in contrast to the esters, the ethers undergo an easy solvolysis in acid media to obtain from compound A (S)α-cyano-3-phenoxy-benzyl alcohol and from compound B (R)α-cyano-3-phenoxy-benzyl alcohol with the alcohols being obtained with retention of their configuration and without undergoing chemical change. The process of the invention with the acid solvolysis permits one to effect resolution of chiral cyano-hydrins. When applied to (RS)α-cyano-3-phenoxy-benzyl alcohol, it permits the obtaining of optical antipodes of the cyanohydrin in the (S) form which is of particular interest since the esters of the (S) alcohol with various propane carboxylic acids and α- substituted arylacetic acids are useful as extremely powerful insecticides.

In the following examples there are described several preferred examples to illustrate the invention. However, it is to be understood that the invention is not intended to be limited to the specific embodiments.

EXAMPLE 1

A mixture of 22.53 g of (R,S)α-cyano-3-phenoxy-benzyl alcohol, 9.46 g of the lactone of cis 2,2-dimethyl-3S-(dihydroxymethyl)-cyclopropane-1R-carboxylic acid and 0.15 g of p-toluene sulfonic acid monohydrate was heated to 80° C. under a reduced pressure of $10^{-2}$mm Hg for 2 hours while removing the water to obtain 30.7 g of residue. The latter was dissolved in 100 ml of methylene chloride and 400 ml of isopropyl ether and the organic solution was washed with 2 N sodium hydroxide solution, with water, with 0.1 N aqueous hydrochloric acid and finally with water. The aqueous wash waters were extracted with a mixture of methylene chloride and isopropyl ether and the combined organic phases were dried and filtered. The filtrate was evaporated to dryness under reduced pressure and the 27.8 g of residue were dissolved in 56 ml of ethanol. 150 ml of aqueous saturated sodium bisulfite solution were added thereto and a precipitate appeared. The mixture was stirred for 90 minutes and 50 ml of ethyl acetate were added thereto. The mixture was filtered and the insolubles were washed with ethylacetate and water. The filtrate was allowed to stand. The aqueous phase was decanted and the organic phase was washed with aqueous sodium chloride solution, was dried and filtered. The filtrate was evaporated to dryness under reduced pressure to obtain 18,4 g of a raw mixture of (1R,5S) 6,6-dimethyl-4(R)-[(S)-cyano-(3'-phenoxy-phenyl)-methoxy]-3-oxa-bicyclo-(3-1-0)-hexan-2-one and (1R, 5S) 6,6-dimethyl-4(R)-[(R)-cyano-(3'-phenoxy-phenyl)-methoxy]-3-oxa-bicyclo-(3-1-0)-hexan-2-one which was used as such for the next step.

The said 18.4 g of the mixture were dissolved at 45° C. in 75 ml of isopropanol and the temperature was allowed to return to 30° C. Then 7.5 ml of triethylamine were added thereto with stirring and the mixture was stirred for 17 hours at 22° C. The mixture was vacuum filtered and the recovered product was washed with isopropanol, dried and crystallized from 35 ml of isopropanol to obtain 10.66 g of (1R,5S) 6,6-dimethyl-4(R)-[(S)-cyano-(3'-phenoxy-phenyl)-methoxy]-3-oxa-bicyclo-(3-1-0)-hexan-3-one melting at 126° C. and having a specific rotation of $[\alpha]_D^{20} = -71°$ (c=1% in benzene).

U.V. Spectrum (ethanol)

| | |
|---|---|
| Inflex. at 226 nm | $E_1^1 = 319$ |
| Inflex. at 267 nm | $E_1^1 = 52$ |
| Inflex. at 271 nm | $E_1^1 = 56$ |
| Max. at 270 nm | $E_1^1 = 60$ |

-continued

| | |
|---|---|
| Inflex. at 280 nm | $E_1^1 = 48$ |

RMN Spectrum (deuterochloroform)

peaks at 1.18–1.23 ppm (hydrogens of geminal methyls); at 1.98–2.08 and 2.15–2.25 ppm (hydrogens of cyclopropyl); at 5.53–5.56 ppm (hydrogen of carbon having CN attached and of 4-hydrogen).

EXAMPLE 2

1 g of p-toluene sulfonic acid monohydrate and 10 g of (1R,5S) 6,6-dimethyl-4(R)-[(S)-cyano-(3'-phenoxyphenyl)-methoxy]-3-oxa-bicyclo-(3-1-0)-hexan-2-one were added to 100 ml of dioxane and 50 ml of water and the mixture was refluxed for 23 hours. The mixture was concentrated under reduced pressure to half of its original volume and ether was added thereto. The decanted ether phase was washed with water, dried and filtered and the filtrate was evaporated to dryness under reduced pressure. The 9.5 g of residue were chromatographed over silica gel and was eluted with a 9-1 benzene-ethyl acetate mixture to obtain 6.1 g of (S)α-cyano-3-phenoxy-benzyl alcohol with a specific rotation of $[\alpha]_D^{20} = -16.5°$ (c=0.8% in benzene).

RMN Spectrum (deuterochloroform)

peaks at 3.25 ppm (hydrogens of alcohol); at 5.42 ppm (hydrogen on carbon attached to —CN).

Various modifications of the process of the invention may be made without departing from the spirit or scope thereof and it should be understood that the invention is intended to be limited only as defined in the appended claims.

We claim:

1. A process for the preparation of (1R,5S) 6,6-dimethyl-4-(R)[(S)-cyano-(3'-phenoxy-phenyl)-methoxy]-3-oxa-bicyclo-(3-1-0)-hexan-2-one comprising treating a mixture of (1R,5S) 6,6-dimethyl-4(R)-[(S)-cyano(3'-phenoxy-phenyl)-methoxy]-3-oxa-bicyclo-(3-1-0)-hexan-2-one and (1R,5S) 6,6-dimethyl-4(R)-[(R)-cyano-3'-phenoxy-phenyl)-methoxy]-3-oxa-bicyclo-(3-1-0)-hexan-2-one with a basic agent wherein the basic agent is selected from the group consisting of ammonium hydroxide, triethylamine, diethylamine, morpholine, piperidine and pyrrolidine or catalytic amounts of an alkali metal hydroxide, an alkali metal hydride, an alkali metal alkanolate or an alkali metal amide in an organic solvent in which (1R,5S) 6,6-dimethyl-4(R)-[(S)-cyano-(3'-phenoxy-phenyl)-methoxy]-3-oxa-bicyclo-(3-1-0)-hexan-2-one is insoluble and recovering the latter.

2. The process of claim 1 wherein the basic agent is triethylamine.

3. The process of claim 1 wherein the solvent is a lower alkanol.

4. The process of claim 1 wherein the solvent is isopropanol.

* * * * *